United States Patent

Herzig et al.

[11] Patent Number: 5,942,604
[45] Date of Patent: Aug. 24, 1999

[54] AZO DYE MIXTURES

[75] Inventors: Paul Herzig; Antoine Clément, both of Basel; Romeo Dreier, Fehren; Alfons Arquint, Basel, all of Switzerland

[73] Assignee: Ciba Specialty Chemicals Corporation, Tarrytown, N.Y.

[21] Appl. No.: 09/027,479

[22] Filed: Feb. 20, 1998

[30] Foreign Application Priority Data

Feb. 21, 1997 [CH] Switzerland ............................ 409/97

[51] Int. Cl.⁶ ...................... C09B 67/22; C09B 41/00; C07C 233/43; C07C 219/06
[52] U.S. Cl. ...................... 534/581; 534/852; 534/854; 534/DIG. 1; 560/22; 8/639; 8/922
[58] Field of Search ............... 8/639, 922; 534/581, 534/852, 854; 560/22

[56] References Cited

U.S. PATENT DOCUMENTS

| | | | |
|---|---|---|---|
| 2,373,700 | 4/1945 | McNally et al. | 534/852 |
| 3,406,165 | 10/1968 | Kruckenberg et al. | 534/854 |
| 3,637,652 | 1/1972 | Fishwick | 534/852 |
| 4,743,269 | 5/1988 | Haebler et al. | 8/639 |
| 5,324,747 | 6/1994 | Carson et al. | 560/22 X |
| 5,550,217 | 8/1996 | Trottmann | 534/832 |
| 5,569,751 | 10/1996 | Buhler | 534/850 |
| 5,688,288 | 11/1997 | Akatani et al. | 8/639 |

FOREIGN PATENT DOCUMENTS

| | | |
|---|---|---|
| 0439054 | 7/1991 | European Pat. Off. |
| 0685531 | 12/1995 | European Pat. Off. |
| 55-116754 | 8/1980 | Japan. |

OTHER PUBLICATIONS

Chem. Abst. 115:258285t (1991).
Ito et al., Chemical Abstracts, 105:42503, 1986.
Mitsui Toatsu Chemicals, Chemical Abstracts, 104:7136, 1986.
Chemical Abstract., 94:67273, for JP551167754, 1981.

*Primary Examiner*—Fiona T. Powers
*Attorney, Agent, or Firm*—David R. Crichton

[57] ABSTRACT

A dye mixture, which comprises as component (A) a dye of formula

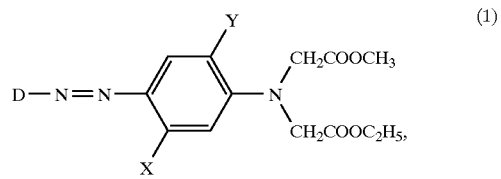

as component (B) a dye of formula

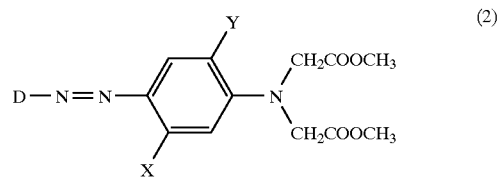

and/or as component (C) a dye of formula

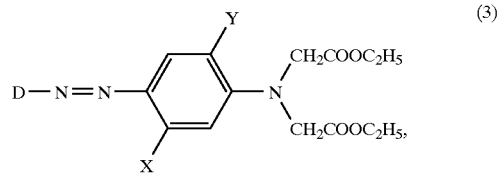

wherein D, X and Y are as defined in the specification. These dyes are particularly suitable for dyeing polyester fiber textile material.

11 Claims, No Drawings

AZO DYE MIXTURES

The present invention relates to mixtures of azo dyes, to their preparation and to their use for dyeing or printing semi-synthetic or synthetic hydrophobic fibre materials.

Azo dyes and their use for dyeing semi-synthetic or synthetic hydrophobic fibre materials are known. However, it has been found that these dyes do not always fully meet the highest demands, in particular as regards fastness to thermomigration. There is therefore a need for novel dyes or dye mixtures which provide dyeings or prints which are very fast to thermomigration and which have good exhaust, build-up or washing properties.

Surprisingly, it has now been found that the novel mixtures substantially fulfill the above criteria.

Accordingly, this invention relates to a dye mixture, which comprises as component (A) a dye of formula

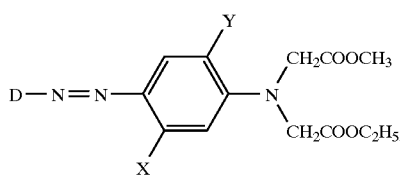

as component (B) a dye of formula

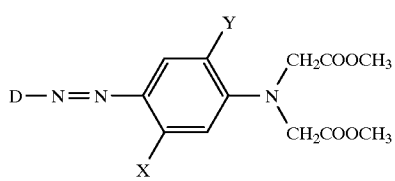

and/or as component (C) a dye of formula

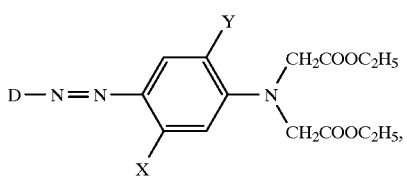

wherein
D is in each case the radical of a diazo component of the benzene, naphthalene, diphenyl, azobenzene, thiophene, benzothiazole, benzisothiazole, thiazole, thiadiazole, indazole, benzotriazole, pyrazole, anthraquinone, hydroxynaphthoic acid imide, chromone or diphenylene oxide series,
X is in each case hydrogen, halogen, $CF_3$, $R_3$, $OR_3$, $NH-CO-R_7$, $NH-CO-OR_8$, $NH-SO_2-R_7$ or $NHCO-NR_4R_5$, wherein $R_3$ is $C_1-C_6$alkyl, $R_4$ and $R_5$ are each independently of the other hydrogen, $C_1-C_4$alkyl or $C_1-C_4$alkoxy-$C_2-C_4$alkyl, $R_7$ is hydrogen, $C_1-C_6$alkyl, $C_1-C_4$alkoxy-$C_1-C_4$alkyl or phenyl, and $R_8$ is $C_1-C_6$alkyl or $C_1-C_4$alkoxy-$C_2-C_4$alkyl, and
Y is in each case hydrogen, halogen, methoxy, ethoxy or $O(CH_2)_n-OR_9$, wherein $R_9$ is hydrogen, methyl or $CH_2CH_2CN$, and n is an integer from 1 to 6.

In this invention, alkyl radicals will be understood as being generally straight-chain, branched or cyclic alkyl groups.

$R_3$, $R_7$ and $R_8$ defined as $C_1-C_6$alkyl are typically methyl, ethyl, propyl, i-propyl, n-butyl, i-butyl, sec-butyl, tert-butyl, amyl, tert-amyl (1,1-dimethylpropyl), 1,1,3,3-tetramethylbutyl, hexyl, 1-methylpentyl, neopentyl, cyclopentyl, cyclohexyl, as well as the corresponding isomers.

$R_4$ and $R_5$ defined as $C_1-C_4$alkyl are methyl, ethyl, propyl, i-propyl, n-butyl, i-butyl, sec-butyl, tert-butyl.

$R_4$, $R_5$, $R_7$ and $R_8$ defined as $C_1-C_4$alkoxy-$C_2-C_4$alkyl are typically methoxyethyl, methoxypropyl, methoxybutyl, ethoxypropyl, ethoxy-iso-propyl, propoxyethyl, isobutoxypropyl or n-butoxyethyl.

X defined as halogen is fluoro, bromo, iodo or, preferably, chloro.

Y defined as halogen is fluoro, bromo, iodo or, preferably, chloro.

In preferred dye mixtures, D is a radical of formula

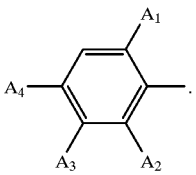

In this formula
$A_1$ is hydrogen, halogen, $SO_2R_3$, $CF_3$ or CN,
$A_2$ is hydrogen, halogen, $NO_2$ or CN,
$A_3$ is hydrogen or halogen, and
$A_4$ is hydrogen, halogen, nitro, $R_3$, $NHCOR_3$ or $OR_3$, wherein $R_3$ has the meaning cited above.

In particularly useful dye mixtures, X is halogen, $R_3$ or, preferably, the radical $NH-CO-R_7$, wherein $R_3$ and $R_7$ have the meaning cited above and are preferably each independently of the other methyl, ethyl or isopropyl.

In particularly useful dye mixtures, D is a radical of formula (4), wherein $A_1$ is hydrogen, halogen or CN, $A_2$ is hydrogen, halogen, CN or nitro, $A_3$ is hydrogen, and $A_4$ is nitro.

Very particularly useful dye mixtures are those, wherein D is the radicals of formula

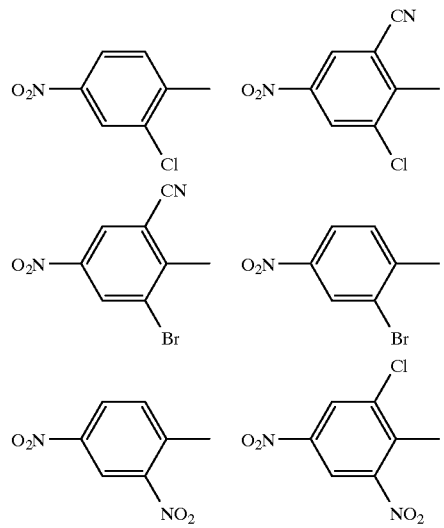

-continued

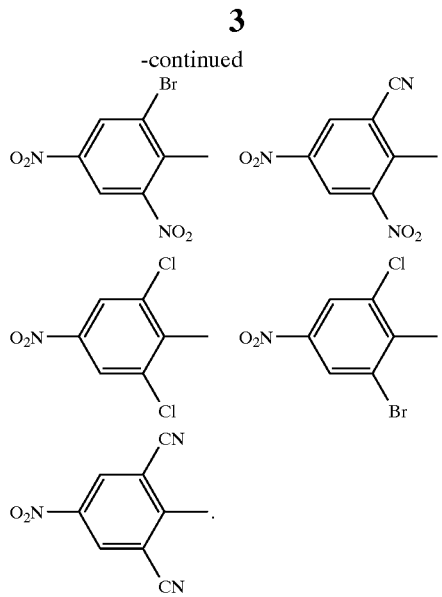

The ratio of components (A) and (B), or of components (A) and (C), in the dye mixtures of this invention can vary within wide limits, for example from 99:1 up to 1:99, preferably from 95:5 up to 5:95, more preferably from 90:10 up to 10:90.

The dye components (B) and (C) of formulae (2) and (3) are known, inter alia, from EP-A-0 555 179. The dye component (A) of formula (1) is novel.

This invention also relates to the process for the preparation of the novel dye mixtures.

These are prepared, for example, by diazotising a compound of formula D—$NH_2$, preferably a compound of formula

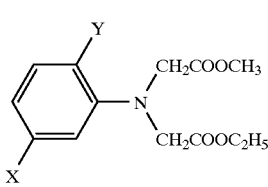 (4a)

and coupling the diazonium compound so obtained to a coupling component mixture comprising the coupling components of formulae

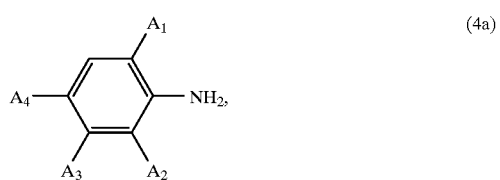 (5)

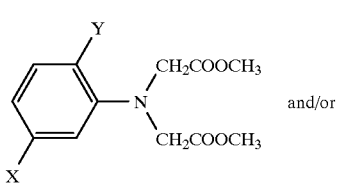 (6) and/or

-continued

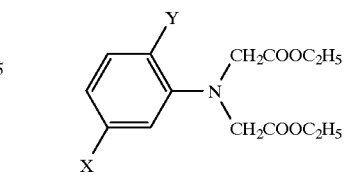 (7)

wherein D, $A_1$, $A_2$, $A_3$, $A_4$, X and Y have the meanings cited above.

The diazotisation of the compound of formula (4a) is carried out in per se known manner, for example with sodium nitrite in acid, typically hydrochloric or sulfuric acid, aqueous medium. The diazotisation can, however, also be carried out with other diazotising agents, conveniently with nitrosylsulfuric acid. The reaction medium of the diazotisation may contain an additional acid, typically phosphoric acid, sulfuric acid, acetic acid, propionic acid, hydrochloric acid or mixtures of these acids, for example mixtures of propionic acid and acetic acid. The diazotisation is conveniently carried out in the temperature range from −10 to 30° C., for example from −10° C. to room temperature.

The coupling of the diazotised compound of formula (4a) to the mixture of the coupling components of formulae (5), (6) and/or (7) is also carried out in known manner, for example in acid, aqueous or aqueous-organic medium, preferably in the temperature range from −10 to 30° C., most preferably below 10° C. Suitable acids include hydrochloric acid, acetic acid, propionic acid, sulfuric acid or phosphoric acid.

The diazo components of formula (4) are known and can be prepared in per se known manner.

The mixture of the coupling components of formulae (5), (6) and (7) is novel and is also an object of this invention.

The coupling components of formulae (6) and (7) are known per se and can be prepared in a manner known per se. The coupling component of formula

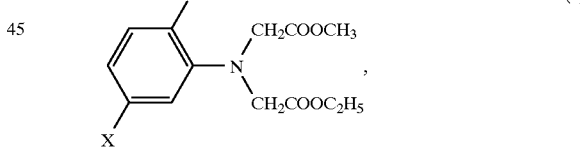 (5)

wherein

X and Y have the meanings and preferred meanings cited above, is novel.

This invention also relates to the process for the preparation of the coupling component mixture comprising the coupling components of formulae

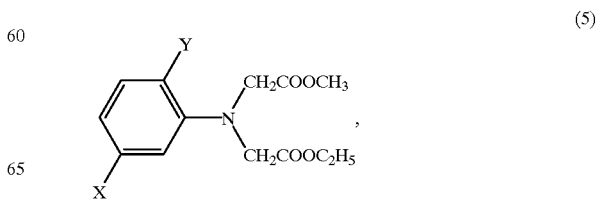 (5)

-continued

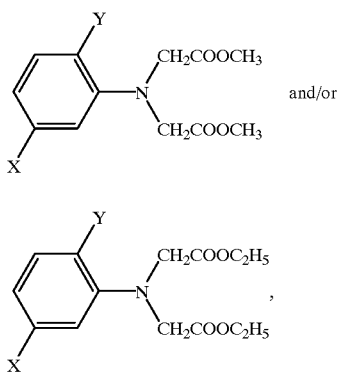

and/or wherein
X and Y have the meanings and preferred meanings cited above, which process comprises reacting an aniline of formula

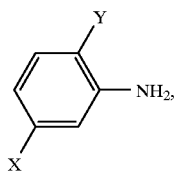

wherein
X and Y have the meaning given above, with a mixture of methyl chloroacetate and ethyl chloroacetate in a ratio of 95:5 to 5:95. This reaction is preferably carried out at elevated temperature, for example in the range from 60 to 130° C., preferably from 105 to 125° C., in the presence of an acid acceptor, such as sodium acetate, sodium bromide or soda, if appropriate in an inert solvent.

The novel dye mixtures can be used as dyes for dyeing or printing semi-synthetic and, in particular, synthetic hydrophobic fibre materials, especially textile materials. Textile blends containing such semi-synthetic or synthetic hydrophobic textile materials can also be dyed or printed using the novel compounds.

Suitable semi-synthetic textile materials are in particular cellulose secondary acetate and cellulose triacetate.

Synthetic hydrophobic textile materials consist primarily of linear aromatic polyesters, typically those from terephthalic acid and glycols, especially ethylene glycol or condensates of terephthalic acid and 1,4-bis(hydroxymethyl) cyclohexane; of polycarbonates, typically those from α,α-dimethyl-4,4-dihydroxydiphenylmethane and phosgene, or of fibres based on polyvinyl chloride and polyamide.

The novel compounds are applied to the textile materials by known dyeing methods. Typically, polyester fibre materials are dyed from an aqueous dispersion by the exhaust process in the presence of customary anionic or nonionic dispersants and in the presence or absence of customary swelling agents (carriers) in the temperature range from 80 to 140° C. Cellulose secondary acetate is preferably dyed at a temperature from about 65 to 85° C., and cellulose triacetate at temperatures of up to 115° C.

The novel dyes do not stain wool and cotton simultaneously present in the dyebath or effect only minor staining (very good resist), so that they can also readily be used for dyeing polyester/wool and polyester/cellulose blends.

The novel dyes are suitable for dyeing by the thermosol process, for exhaust dyeing and for printing.

The textile material may be in any form of presentation, such as fibre, thread or nonwoven fabric, or wovens or knitgoods.

It is expedient to convert the novel dye mixtures, before use, into a dye formulation. This is done by milling the dye mixture to an average particle size of 0.1 to 10 microns. Milling can be carried out in the presence of dispersants. Typically, the dried dye mixture is milled with a dispersant, or kneaded in paste form with a dispersant, and thereafter dried under vacuum or by spray drying. Printing pastes and dyebaths can be prepared by adding water to the formulations so obtained.

The customary thickeners will be used for printing, for example modified or nonmodified natural products, such as alginates, British gum, gum arabic, crystal gum, carob bean gum, tragacanth, carboxymethylcellulose, hydroxyethylcellulose, starch or synthetic products, including polyacrylamides, polyacrylic acid or copolymers thereof, or polyvinyl alcohols.

The cited materials, especially polyester material, are dyed with the novel dyes in level shades having very good end-use properties, in particular good fastness to light, thermofixation, pleating, chlorinating and good fastness to weat treatments, such as fastness to water, sweat and washing; and the dyeings are also distinguished by excellent fastness to rubbing. To be highlighted in particular is the good thermomigration fastness of the dyeings obtained.

The novel dyes can also be readily used for obtaining mixed shades in conjunction with other dyes.

In addition, the novel dye mixtures are also very suitable for dyeing hydrophobic textile material from supercritical $CO_2$.

Further objects of the invention are the aforementioned use of the dye mixtures of this invention and a process for dyeing or printing semi-synthetic or synthetic hydrophobic fibre material, preferably textile material, which comprises applying the novel dye mixture to said material or incorporating it therein. The cited hydrophobic fibre material is preferably polyester textile material. Other substrates which can be treated by the process of this invention and preferred process conditions have been discussed above in the more detailed description of the use of the novel dyes.

This invention also relates to the hydrophobic fibre material, preferably polyester textile material, which is dyed or printed by the cited process.

The novel dye mixtures are also suitable for modern recording processes, for example thermotransfer printing.

The invention is illustrated in more detail by the following Examples. Parts and percentages are by weight, unless otherwise stated. Temperatures are given in degrees Celsius. The relationship between parts by weight and parts by volume is the same as that of the gramme and the cubic centimeter.

EXAMPLE 1

In a reaction vessel, 50 parts by weight of 3-aminoacetanilide are added to a mixture consisting of 98 parts by weight of methyl chloroacetate and 110 parts by weight of ethyl chloroacetate at room temperature. Subsequently, 58 parts by weight of anhydrous sodium carbonate and 5.2 parts by weight of sodium bromide are added. The reaction mixture is then slowly heated over 3 hours to 115° C. and is stirred for 9 hours at this temperature. After this time, the reaction mixture is cooled to 25° C. and charged with 320 parts by weight of cold water. The resultant emulsion is stirred until the salt, which has been added earlier, is completely dissolved. The organic phase is then separated using a separating funnel and the mixture of methyl chloroacetate and ethyl chloroacetate is distilled therefrom under vacuum. The distillation residue consists of a mixture of about 50% methyl/ethyl ester of formula

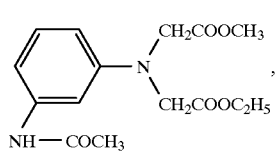
(10a)

about 25% of dimethyl ester of formula

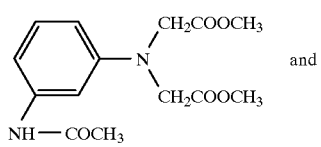 and
(10b)

about 25% of diethyl ester of formula

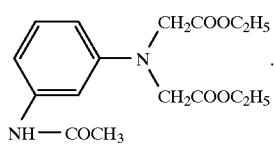
(10c)

The procedure of Example 1 is repeated, but replacing an equimolar mixture of methyl chloroacetate and ethyl chloroacetate with a mixture of methyl chloroacetate and ethyl chloroacetate in the ratio indicated in Table 1, resulting in a mixture having the following composition of the esters of formulae (10a) to (10c):

TABLE 1

| Example No. | Ratio (mol %) methyl chloro-acetate:ethyl chloroacetate | Composition of the mixture of the compounds of formulae (10a):(10b):(10c) |
|---|---|---|
| 2 | 75:25 | 37:56:7 |
| 3 | 80:20 | 35:60:5 |
| 4 | 85:15 | 26:71:3 |
| 5 | 90:10 | 22:77:1 |
| 6 | 25:75 | 37:7:56 |
| 7 | 20:80 | 35:5:60 |
| 8 | 15:85 | 26:3:71 |
| 9 | 10:90 | 22:1:77 |

In a manner analogous to that of Example 1, it is possible to replace 3-aminoacetanilide with the following amines listed in Table 2:

TABLE 2

$$\text{(structure with Y, X, NH}_2\text{)}$$

| Example No. | Y | X |
|---|---|---|
| 10 | H | NHCOCH$_2$CH$_3$ |
| 11 | H | NHCOCH(CH$_3$)$_2$ |
| 12 | H | NHCOCH$_2$CH$_2$CH$_3$ |
| 13 | OCH$_3$ | NHCOCH$_3$ |
| 14 | OCH$_2$CH$_3$ | NHCOCH$_3$ |
| 15 | OCH$_2$CH$_2$OCH$_3$ | NHCOCH$_3$ |
| 16 | OCH$_3$ | NHCOCH$_2$CH$_3$ |
| 17 | Cl | NHCOCH$_3$ |
| 18 | Cl | NHCOCH$_2$CH$_3$ |
| 19 | H | CH$_3$ |
| 20 | H | Cl |

In a manner analogous to that of Examples 2 to 9, it is possible to replace 3-aminoacetanilide also with the amines listed in Table 2.

EXAMPLE 21

48.5 Parts by weight of 2-chloro-4-nitroaniline are made into a slurry in 100 parts by weight of water and are then charged with 92 parts by weight of 32% HCl and stirred for 2 hours at 20–30° C. The reaction mixture is cooled to 0° C. by adding 125 parts by weight of ice. Subsequently, 81 parts by weight of a 24.1% G/G sodium nitrite solution is added dropwise over 30 minutes at 0–5° C. and this mixture is stirred for 1 hour at a small excess of nitrite which, if required, is corrected with sulfaminic acid. The resultant diazo solution is then added dropwise over 1.5 hours to a solution of 88 parts by weight of the coupling component of Example 1, dissolved in 230 parts by weight of anhydrous acetic acid, the reaction temperature being kept at 0–15° C. by addition of 400 parts by weight of ice. After the addition of the diazo solution is complete, the reaction mixture is stirred for 1 hour. The precipitated dye is collected by suction filtration, washed with water and dried, giving a scarlet dye mixture of the following composition:

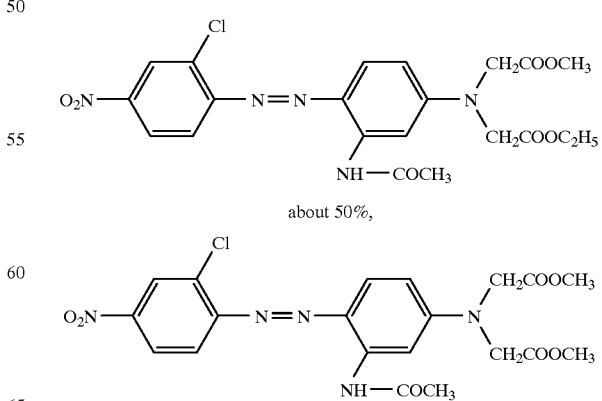

about 50%, about 25% and

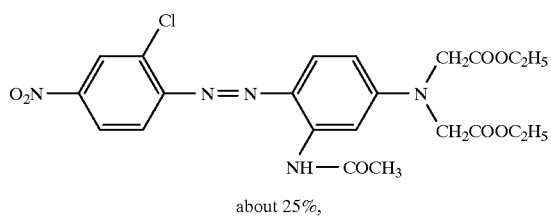

about 25%, which dyes polyester in a brilliant scarlet shade having good fastness properties, in particular fastness to thermomigration and light.

The following mixtures listed in Table 3 are prepared in a manner analogous to that of Example 21 and also dye polyester in brilliant shades having good fastness properties, in particular fastness to thermomigration and light:

TABLE 3

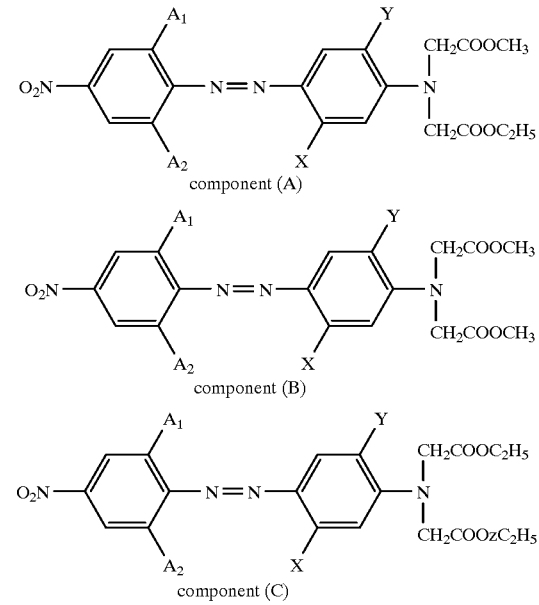

component (A)

component (B)

component (C)

| Ex. No. | $A_1$ | $A_2$ | Y | X | Ratio methyl/ethyl chloroacetate (mol %) | Component A:B:C | Colour |
|---|---|---|---|---|---|---|---|
| 22 | Cl | H | H | NHCOCH$_3$ | 85/15 | 26:71:3 | scarlet |
| 23 | CN | H | H | NHCOCH$_3$ | 50/50 | 50:25:25 | red |
| 24 | CN | Br | H | NHCOCH$_3$ | 85/15 | 26:71:3 | violet |
| 25 | CN | Cl | H | NHCOCH$_3$ | 85/15 | 26:71:3 | violet |
| 26 | Cl | Cl | H | NHCOCH$_3$ | 50/50 | 50:25:25 | brown |
| 27 | CN | NO$_2$ | H | NHCOCH$_3$ | 75/25 | 37:56:7 | violet |
| 28 | Cl | NO$_2$ | OCH$_3$ | NHCOCH$_3$ | 85/15 | 26:71:3 | navy |
| 29 | CN | CN | H | NHCOCH$_3$ | 50/50 | 50:25:25 | violet |
| 30 | H | NO$_2$ | H | NHCOCH$_3$ | 50/50 | 50:25:25 | red |
| 31 | H | CN | H | CH$_3$ | 50/50 | 50:25:25 | red |
| 32 | H | CN | H | NHCOC$_2$H$_5$ | 50/50 | 50:25:25 | red |
| 33 | H | Cl | H | CH$_3$ | 75/25 | 37:56:7 | brown |
| 34 | Br | NO$_2$ | H | CH$_3$ | 25/75 | 37:7:56 | bordeaux |
| 35 | H | NO$_2$ | H | CH$_3$ | 50/50 | 50:25:25 | scarlet |
| 36 | Br | NO$_2$ | H | Cl | 50/50 | 50:25:25 | brown |
| 37 | H | Cl | H | NHCOC$_2$H$_5$ | 75/25 | 37:56:7 | scarlet |
| 38 | H | H | H | NHCOCH$_3$ | 90/10 | 22:77:1 | orange |
| 39 | CN | Cl | H | CH$_3$ | 50/50 | 50:25:25 | bordeaux |
| 40 | Cl | NO$_2$ | H | NHCOCH$_3$ | 50/50 | 50:25:25 | ruby |
| 41 | Br | Br | H | NHCOCH$_3$ | 50/50 | 50:25:25 | brown |
| 42 | Cl | NO$_2$ | OCH$_3$ | NHCOC$_2$H$_5$ | 85/15 | 26:71:3 | navy |
| 43 | Cl | NO$_2$ | OC$_2$H$_5$ | NHCOCH$_3$ | 85/15 | 26:71:3 | navy |
| 44 | Br | NO$_2$ | OCH$_3$ | NHCOCH$_3$ | 85/15 | 26:71:3 | navy |
| 45 | H | NO$_2$ | OCH$_3$ | NHCOCH$_3$ | 85/15 | 26:71:3 | navy |
| 46 | Cl | NO$_2$ | OC$_2$H$_4$OCH$_3$ | NHCOCH$_3$ | 85/15 | 26:71:3 | navy |
| 47 | Cl | H | Cl | NHCOCH$_3$ | 50/50 | 50:25:25 | scarlet |
| 48 | CN | H | C | NHCCCH$_3$ | 50/50 | 50:25:25 | red |
| 49 | CN | Cl | H | NHCOCH(CH$_3$)$_2$ | 50/50 | 50:25:25 | violet |

What is claimed is:

1. A dye mixture, which comprises as component (A) a dye of formula

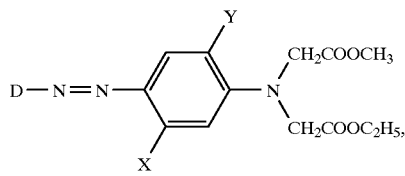
(1)

as component (B) a dye of formula

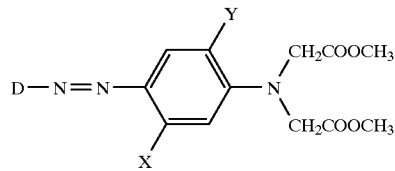
(2)

and/or as component (C) a dye of formula

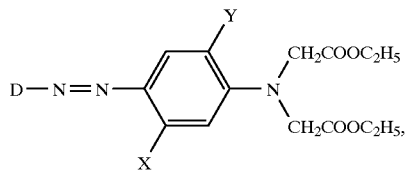
(3)

wherein
D is in each case the radical of a diazo component of the benzene, naphthalene, diphenyl, azobenzene, thiophene, benzisothiazole, thiazole, thiadiazole, indazole, benzotriazole, pyrazole, anthraquinone, hydroxynaphthoic acid imide, chromone or diphenylene oxide series,
X is in each case hydrogen, halogen, $CF_3$, $R_3$, $OR_3$, $NH-CO-R_7$, $NH-CO-OR_8$, $NH-SO_2-R_7$ or $NHCO-NR_4R_5$, wherein $R_3$ is $C_1-C_6$alkyl, $R_4$ and $R_5$ are each independently of the other hydrogen, $C_1-C_4$alkyl or $C_1-C_4$alkoxy-$C_2-C_4$alkyl, $R_7$ is hydrogen, $C_1-C_6$alkyl, $C_1-C_4$alkoxy-$C_1-C_4$alkyl or phenyl, and $R_8$ is $C_1-C_6$alkyl or $C_1-C_4$alkoxy-$C_2-C_4$alkyl, and Y is in each case hydrogen, halogen, methoxy, ethoxy or $O(CH_2)_n-OR_9$, wherein $R_9$ is hydrogen, methyl or $CH_2CH_2CN$, and n is an integer from 1 to 6.

2. A dye mixture according to claim 1, wherein D is in each case a radical of formula

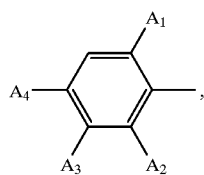
(4)

wherein $A_1$ is hydrogen, halogen, $SO_2R_3$, $CF_3$ or CN, $A_2$ is hydrogen, halogen, $NO_2$ or CN, $A_3$ is hydrogen or halogen, $A_4$ is hydrogen, halogen, nitro, $R_3$, $NHCOR_3$ or $OR_3$, and $R_3$ is $C_1-C_6$alkyl.

3. A dye mixture according to either claim 1 or claim 2, wherein X is halogen, $R_3$ or a radical $NH-CO-R_7$, $R_3$ is $C_1-C_6$alkyl and $R_7$ is hydrogen, $C_1-C_6$alkyl, $C_1-C_4$alkoxy-$C_1-C_4$alkyl or phenyl.

4. A dye mixture according to claim 2, wherein $A_1$ is hydrogen, halogen or CN, $A_2$ is hydrogen, halogen, CN or nitro, $A_3$ is hydrogen and $A_4$ is nitro.

5. A dye mixture according to claim 2, wherein D is the radicals of formula

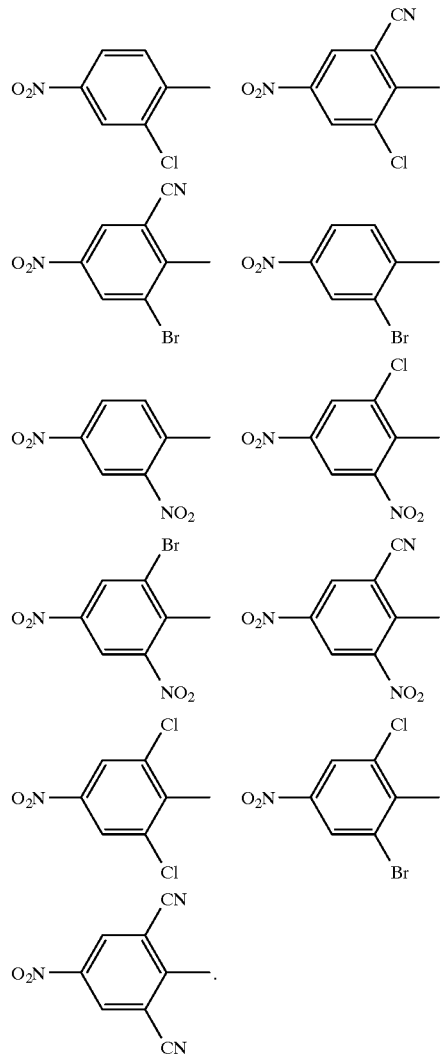

6. A dye mixture according to claim 2, wherein X is halogen, $R_3$ or a radical $NH-CO-R_7$, $R_3$ is $C_1-C_6$alkyl and $R_7$ is hydrogen, $C_1-C_6$alkyl, $C_1-C_4$alkoxy-$C_1-C_4$alkyl or phenyl.

7. A process for the preparation of the dye mixture according to claim 2, which comprises diazotising a compound of formula

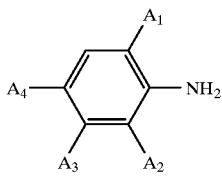
(4a)

and coupling the diazonium compound so obtained to a coupling component mixture comprising the coupling components of formulae

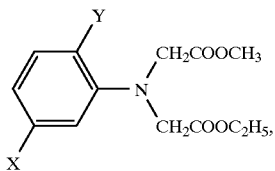
(5)

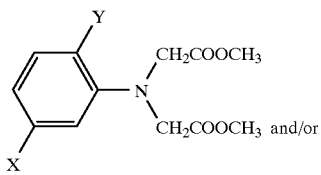
(6)

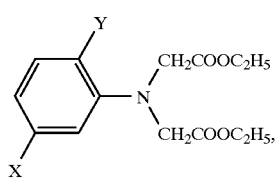
(7)

wherein $A_1$ is hydrogen, halogen, $SO_2R_3$, $CF_3$ or CN, $A_2$ is hydrogen, halogen, $NO_2$ or CN, $A_3$ is hydrogen or halogen, $A_4$ is hydrogen, halogen, nitro, $R_3$, $NHCOR_3$ or $OR_3$, and $R_3$ is $C_1$–$C_6$alkyl, X is in each case hydrogen, halogen, $CF_3$, $R_3$, $OR_3$, NH—CO—$R_7$, NH—CO—$OR_8$, NH—$SO_2$—$R_7$ or NHCO—$NR_4R_5$, wherein $R_3$ is $C_1$–$C_6$alkyl, $R_4$ and $R_5$ are each independently of the other hydrogen, $C_1$–$C_4$alkyl or $C_1$–$C_4$alkoxy-$C_2$–$C_4$alkyl, $R_7$ is hydrogen, $C_1$–$C_6$alkyl, $C_1$–$C_4$alkoxy-$C_1$–$C_4$alkyl or phenyl, and $R_8$ is $C_1$–$C_6$alkyl or $C_1$–$C_4$alkoxy-$C_2$–$C_4$alkyl, and Y is in each case hydrogen, halogen, methoxy, ethoxy or $O(CH_2)_n$—$OR_9$, wherein $R_9$ is hydrogen, methyl or $CH_2CH_2CN$, and n is an integer from 1 to 6.

8. A coupling component mixture, which comprises the compounds of formulae

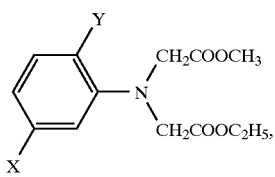
(5)

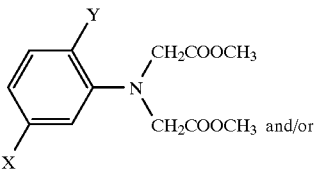
(6)

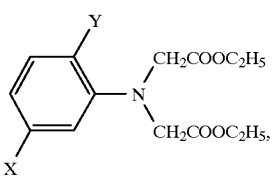
(7)

wherein X is in each case hydrogen, halogen, $CF_3$, $R_3$, $OR_3$, NH—CO—$R_7$, NH—CO—$OR_8$, NH—$SO_2$—$R_7$ or NHCO—$NR_4R_5$, wherein $R_3$ is $C_1$–$C_6$alkyl, $R_4$ and $R_5$ are each independently of the other hydrogen, $C_1$–$C_4$alkyl or $C_1$–$C_4$alkoxy-$C_2$–$C_4$alkyl, $R_7$ is hydrogen, $C_1$–$C_6$alkyl, $C_1$–$C_4$alkoxy-$C_1$–$C_4$alkyl or phenyl, and $R_8$ is $C_1$–$C_6$alkyl or $C_1$–$C_4$alkoxy-$C_2$–$C_4$alkyl, and Y is in each case hydrogen, halogen, methoxy, ethoxy or $O(CH_2)_n$—$OR_9$, wherein $R_9$ is hydrogen, methyl or $CH_2CH_2CN$, and n is an integer from 1 to 6.

9. A process for the preparation of the coupling component mixture according to claim 8, which comprises reacting an aniline of formula

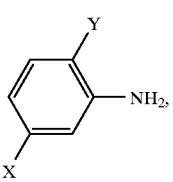
(8)

wherein

X is in each case hydrogen, halogen, $CF_3$, $R_3$, $OR_3$, NH—CO—$R_7$, NH—CO—$OR_8$, NH—$SO_2$—$R_7$ or NHCO—$NR_4R_5$, wherein $R_3$ is $C_1$–$C_6$alkyl, $R_4$ and $R_5$ are each independently of the other hydrogen, $C_1$–$C_4$alkyl or $C_1$–$C_4$alkoxy-$C_2$–$C_4$alkyl, $R_7$ is hydrogen, $C_1$–$C_6$alkyl, $C_1$–$C_4$alko xy-$C_1$–$C_4$alkyl or phenyl, and $R_8$ is $C_1$–$C_6$alkyl or $C_1$–$C_4$alkoxy-$C_2$–$C_4$alkyl, and Y is in each case hydrogen, halogen, methoxy, ethoxy or $O(CH_2)_n$—$OR_9$, wherein $R_9$ is hydrogen, methyl or $CH_2CH_2CN$, and n is an integer from 1 to 6, with a mixture of methyl chloroacetate and ethyl chloroacetate in a ratio of 95:5 to 5:95.

10. A process for dyeing or printing semi-synthetic or synthetic hydrophobic fibre material, which comprises applying the dye mixture claimed in claim 1 to the cited material or incorporating it in this material.

11. A process according to claim 10, wherein the hydrophobic fibre material consists of polyester fibres.

* * * * *